United States Patent [19]

McMichael et al.

[11] Patent Number: 5,753,624

[45] Date of Patent: May 19, 1998

[54] MATERIALS AND METHODS FOR TREATMENT OF PLAQUING DISEASE

[75] Inventors: John McMichael, Delanson, N.Y.; Ellis L. Kline, Pendelton, S.C.

[73] Assignee: Milkhaus Laboratory, Inc., Delanson, N.Y.

[21] Appl. No.: 689,528

[22] Filed: Aug. 8, 1996

Related U.S. Application Data

[63] Continuation-in-part of Ser. No. 249,175, May 25, 1994, abandoned, which is a continuation-in-part of Ser. No. 874,719, Apr. 27, 1992, abandoned, which is a continuation-in-part of Ser. No. 598,383, Oct. 16, 1990, abandoned, which is a continuation-in-part of Ser. No. 514,021, Apr. 27, 1990, abandoned.

[51] Int. Cl.$^6$ .......................... A61K 38/00; A61K 38/55
[52] U.S. Cl. .................. 514/12; 514/21; 424/206.1
[58] Field of Search ................. 514/12, 21; 424/206.1

[56] References Cited

U.S. PATENT DOCUMENTS

| | | | |
|---|---|---|---|
| 4,294,818 | 10/1981 | McMichael et al. | 435/7.24 |
| 4,521,405 | 6/1985 | McMichael et al. | 424/212.1 |
| 4,666,829 | 5/1987 | Colenneo et al. | 435/6 |
| 4,704,273 | 11/1987 | McMichael | 424/130.1 |
| 4,705,685 | 11/1987 | McMichael | 424/212.1 |
| 4,816,416 | 3/1989 | Auerbach | 436/166 |
| 4,880,626 | 11/1989 | McMichael | 424/184.1 |
| 4,912,206 | 3/1990 | Goldgaber et al. | 536/23.5 |
| 5,187,153 | 2/1993 | Cordell et al. | 514/12 |
| 5,223,482 | 6/1993 | Schilling et al. | 514/12 |

FOREIGN PATENT DOCUMENTS

| | | |
|---|---|---|
| WO 88/03951 | 6/1988 | WIPO . |
| WO 90/14841 | 12/1990 | WIPO . |
| WO 91/16819 | 11/1991 | WIPO . |
| WO 95/31996 | 11/1995 | WIPO . |

OTHER PUBLICATIONS

Bahmanyar et al., "Characterization of Antineurofilament Autoantibodies in Creutzfeldt–jakob Disease," *J. Neuropathol. Exp. Neurol.*, 43(4):369–375 (Jul. 1984).

Bahmanyar et al., "Serum Antibodies to Neurofilament Antigens in Patients with Neurological and Other diseases and in Healthy cControls," *J. Neuroimmunol.*, 5:191–196 (1983).

Baudry et al., "Low Levels of Calpain Activity in Chiropera Brain: Implications for Mechanisms of Aging," *Neurobiol. Aging*, 7:255–258 (1986).

Bruce, "Amyloid Plaques in Experimental Scrapie: Factors Influencing the Occurance of Cerebral Amyloid in Inbred Mice," *J. Neuropathol. Exp. Neurol.*, 37:595 (1978).

Bruist et al., "Synthesis of a Site–Specific DNA–Binding Peptide," *Science*, 235:777–780 (Feb. 13, 1987).

Castano et al., "In Vitro Formulation of Amyloid Fibrils from Two Synthetic Peptides of Different Lengths Homologous to Alzheimer's Disease β–Protein," *Biochem. Biophys. Res. Com.*, 141(2):782–789 (Dec. 15, 1986).

Cohen and Calkins, "Electron Microscopic Observations on a Fibrous Component in Amyloid of Diverse Origins," *Nature*, 183:1202–1203 (Apr. 25, 1959).

Cohen and Calkins, "The Isolation of Amyloid Fibrils and a Study of the Effect of Collagenase and Hyaluronidase," *J. Cell Biol.*, 183:481–486 (1964).

Cohen et al., "Analysis of Histology and Staining Reactions of Casein–Induced Amyloidosis in the Rabbit," *Am. J. Pathol.*, 35(5):971–989 (Sep.–Oct. 1959).

Dahl and Bignami, "Immunochemical Cross–Reactivity of Normal Neurofibrils and Aluminum–Induced Neurofibrillary Tangles," *Exp. Neurol.*, 58:74–80 (1978).

Elizan et al., "Antineurofilament Antibodies in Postencephalitic and Idiopathic Parkinson's Disease," *J. Neurol. Sci.*, 59:341–347 (1983).

Gajdusek, "Hypothesis: Interference with Axonal Transport of Neurofilament as a Common Pathogenetic Mechanism in Certain Diseases of the Central Nervous System," *New Eng. J. Med.*, 312(11):714–719 (Mar. 14, 1985).

Ghiso et al., "Alzheimer's Disease Amyloid Precursor Protein is Present in Senile Plaques and Cerebrospinal Fluid: Immunohistochemical and Biochemical Characterization," *Biochem. Biophys. Res. Com.*, 163(1):430–437 (Aug. 30, 1989).

Glenner, "Alzheimer's Disease The Commonest Form of Amyloidosis," *Arch. Pathol. Lab. Med.*, 107:281–282 (Jun. 1983).

Glenner and Wong, "Alzheimer's Disease and Down's Syndrome: Sharing of a Unique Cerebrovascular Amyloid Fibril Protein," *Biochem. Biophys. Res. Com.*, 122(3):1131–1135 (1984).

Goldman et al., "Cytoplasmic Fibers in Mammalian Cells: Cytoskeletal and Contractile Elements," *Ann. Rev. Physiol.*, 41:703–722 (1979).

Griffin et al., "Slow Axonal Transport of Neurofilament Proteins: Impairment by β,β'–Iminodipropionitrile Administration," *Science*, 202:633–635 (Nov. 1978).

Hoffman and Lasek, "The Slow Component of Axonal Transport," *J. Cell. Biol.*, 66:351–366 (1975).

Howard and Pilkington, "Antibodies to fibronectin bind plaques and other structures in Alzheimer's disease and control brain," *Neuroscience Letters*, 118:71–76 (1990).

Iqbal et al., "Chemical Relationship of the Paired Helical Filaments of Alzheimer's Dementia to Normal Human Neurofilaments and Neurotubules," *Brain Res.*, 142:321–332 (1978).

(List continued on next page.)

*Primary Examiner*—Cecilia J. Tsang
*Assistant Examiner*—P. Lynn Touzeau
*Attorney, Agent, or Firm*—Marshall, O'Toole, Gerstein, Murray & Borun

[57] ABSTRACT

Methods and compositions are provided for alleviation of disease states involving plaque formation, such as are manifested in Alzheimer's Disease and other amyloid disorders, and arteriosclerotic disease. Methods for the treatment of herpes virus infections by administration of thimerosal are further provided by the invention.

16 Claims, No Drawings

OTHER PUBLICATIONS

Itagaki, et al., "Presence of T–Cytotoxic Suppressor and Leucocyte Common Antigen Positive Cells in Alzheimer's Disease Brain Tissue," *Neuroscience Letters*, 91:259–264 (1988).

Joachim and Selkoe, "Amyloid Protein in Alzheimer's Disease," *J. Gerontology*, 44:(4):B77–84 (1989).

Jones et al., "Evidence for Active Epstein–Barr Virus Infection in Patients with Persistent, Unexplained Illnesses: Elevated Anti–Early Antigen Antibodies," *Annals of Internal Medicine*, 102:1–6 (Jan. 1985).

Kang et al., "The precursor of Alzheimer's disease amyloid A4 protein resembles a cell–surface receptor," *Nature*, 325:733–736 (Feb. 19, 1987).

Kilbourne, "Inactivated Influenza Virus Vaccines" in *Vaccines*, pp. 420–434, Plotkin et al., Eds., W.B. Saunders Company, Philadelphia (1988).

Knight, "Dopamine–Receptors–Stimulating Autoantibodies: A Possible Cause of Schizophrenia," *Lancet*, 82:1073–1076 (Nov. 13, 1982).

Komaroff, "The [Chronic Mononucleosis] Syndromes," *Hospital Practice*, 71–75 (May 30, 1987).

Lasak, "The Dynamic Ordering of Neuronal Cytoskeletons," *Neurosciences. Res. Prog. Bull.*, 19(1):7–32 (1981).

Lieberman, "The Role of the Rubella Virus In the Chronic Fatigue Syndrome," *Clinical Ecology*, 7(3):51–54 (1990).

Marx, "A New Link in the Brain's Defenses," *Science*, 256:1278–1280 (May 29, 1992).

Marx, "Testing of Autoimmune Therapy Begins," *Science*, 252:27–28 (Apr. 5, 1991).

Masters et al., "Amyloid plaque core protein in Alzheimer disease and Down syndrome," *Proc. Natl. Acad. Sci. USA*, 82:4245–4249 (Jun. 1985).

Melnick et al., "Possible Role of Cytomegalovirus in Atherogenesis," *JAMA*, 263(16):2204–207 (Apr. 25, 1990).

Miller, "A Double–Blind Study of Food Extract Injection Therapy: A Preliminary Report," *Annals of Allergy*, 38:185–191 (Mar. 1977).

Miller, "Influenza: Rapid Relief Without Drugs," *Clinical Medicine*, 81:16–19 (Sep. 1974).

Moos and Solomon, "Psychologic Comparisons Between Women with Rheumatoid Arthritis and their Nonarthritic Sisters," *Psychosom. Med.*, 27(2):135–149 (1965).

Newcombe and Cohen, "Solubility Characteristics of Isolated Amyloid Fibrils," *Biochem. et Biophys. Acta*, 104:480–486 (1965).

Rabins and Folstein, "The Dementia Patient: Evaluation and Care," *Geriatrics*, 38(8):99–117 (Aug. 1983).

Reines, "Early Clinical Trials in Alzheimer's Disease: Selection and Evaluation of Drug Canidates," *Progress in Clin. Biol. Res.*, 1283–1290 (1989).

Samet, Peptides Offer Promise forTtreating Alzheimer's and other Neurodiseases, *Genetic Engineering News*, p. 24 (Jul./Aug. 1991).

Selkoe et al., "Isolation of Low–Molecular–Weight Proteins from Amyloid Plaque Fibers in Alzheimer's disease," *J. Neurochem.*, 46:1820–1834 (1986).

Shacks et al., "Increased Serum IgG4 Levels in Acute Epstein–Barr Viral Mononucleosis," *Annals of Allergy*, 54:284–288 (Apr. 1985).

Shelanski and Liem, "Neurofilaments," *J. Neurochem.*, 33:5–13 (1979).

Snow and Wight, "Proteoglycans in the Pathogenesis of Alzheimer's Disease and Other Amyloidoses," *Neurobio. Aging*, 10:481–497 (1989).

Solomon, "Psychoneuroimmunology: Interactions Between Central Nervous System and Immune System," *J. Neurosci. Res.*, 18:1–9 (1987).

Solomon and Moos, "Emotions, Immunity, and Disease," *Arch. Gen. Psychiatry*, 11:657–674 (Dec. 1964).

Strauss et al., "Persistng Illness and Fatigue in Adults with Evidence of Epstein–Barr Virus Infection," *Annals of Internal Medicine*, 102:7–16 (1985).

Tanzi et al., "Amyloid $\beta$ Protein Gene: cDNA, mRNA Distribution and Genetic Linkage Near the Alzheimer Locus," *Science*, 235:880–884 (Feb. 20, '1987).

Tingle et al., "Prospective Immunological Assessment of Arthritis Induced by Rubella Vaccine," *Infect. Immun.*, 40(1):22–28 (Apr. 1983).

Turnell et al., "Secondary Structure Prediction of Human $SAA_1$ Presumptive Identification of Calcium and Lipid Binding Sites," *Mol. Biol. Med.*, 3:387–407 (1986).

Turnell et al., "X–Ray Scattering and Diffraction by Wet Gels of AA Amyloid Fibrils," *Mol. Biol. Med.*, 3:409–424 (1986).

Wirak et al., "Deposits of Amyloid $\beta$ Protein in the Central Nervous System Transgenic Mice," *Science*, 253:323–325 (Jul. 19, 1991).

Wong et al., "Neuritic plaques and cerebrovascular amyloid in Alzheimer disease are antigenically related," *Proc. Natl. Acad. Sci. USA*, 82:8729–8732 (Dec. 1985).

Yanker et al., "Neurotrophic and Neurotoxic Effects of Amyloid $\beta$ Protein: Reversal by Tachykinin Neuropeptides," *Science*, 250:279–282 (Oct. 12, 1990).

Zurawaki et al., "Activation of Mouse T–Helper Cells Induces Abundant Preproenkephalin mRNA Synthesis," *Science*, 232:772–775 (May 9, 1986).

Allsop, D. et al., "Immunohistochemical Evidence For the Derivation of a Peptide Ligand from the Amyloid Beta–P–rotein Precursor of Alzheimer Disease," *Proc. Natl., Acad. Sci., USA*, 85(8):2790–2794 (Apr., 1988).

DeFeudis, F.V., "Beta–Amyloid Protein in Transgenic Mice," *DN&P*, 4(10):617–619 (Dec., 1991).

Ma J., et al., "Amyloid–associated proteins $\alpha_1$–antichymotrypsin and apolopoprotein E promote assembly of Alzheimer $\beta$–protein into filaments," *Nature*, 372:92–94 (Nov. 3, 1994).

Marx, J., "Alzheimer's Debate Boils Over," *Science* 257:1336–1338 (Sep. 4, 1992).

Pennish, E., "A Molecular Whodunit New Twists in the Alzheimer's Mystery," *Science News*, 145:8–11 (Jan. 1, 1994).

Selkoe, D.J., "In the beginning . . . " *Nature*, 354:432–433 (Dec. 12, 1991).

Whitson, J., et al., "Amyloid Beta Protein Enhances the Survival of Hippocampal Neurons *in Vitro*," *Science*, 243:1488–1490 (Mar. 17, 1989).

Miller, J.B., "Treatment of Active Herpes Virus Infections with Influenza Virus Vaccine", *Annals of Allergy*, 42:295–305 (1979).

Miller, J.B., "Influenza and Herpes Treatment and Responses", *Relief at Last: Neutralization for Food Allergy and Other illnesses* Ch. 27, 239–248 (1987).

Miller, J.B., "The Importance of Herpes Virus Infections and the Ability to Neutralize Them", *Relief at Last: Neutralization for food Allergy and Other illnesses* Ch. 9, 256–263 (1987).

MATERIALS AND METHODS FOR TREATMENT OF PLAQUING DISEASE

This is a continuation-in-part of U.S. application Ser. No. 08/249,175 filed May 25, 1994, now abandoned, which is a continuation-in-part of U.S. application Ser. No. 07/874, 719, filed Apr. 27, 1992, now abandoned, which is a continuation-in-part of U.S. patent application Ser. No. 07/598,383, filed Oct. 16, 1990, now abandoned, which is a continuation-in-part of U.S. application Ser. No. 07/514, 021, filed Apr. 27, 1990, now abandoned.

FIELD OF THE INVENTION

The present invention relates to methods and materials for the treatment of diseases involving plaque formation including arteriosclerotic diseases and hypertension and more specifically to materials and methods for the treatment of atherosclerosis. As a further aspect of the present invention, materials and methods are provided for the treatment of herpes virus infections including but not limited to Herpes simples types 1 and 2, Epstein-Barr virus, cytomegalovirus, Herpes zoster and further for treatment of chronic fatigue syndrome

BACKGROUND OF THE INVENTION

Cellular skeletal systems have three distinct ultrastructural features, microtubules, intermediate filaments, and microfilaments, all of which are fibrous macromolecules associated with the central nervous system (CNS). Neuronal intermediate filaments, defined as neurofilaments (containing amyloid beta protein constructs), are distinct from other intermediate filaments found in the cells of the central nervous system. R. D. Goldman, A. Milstead, J. A. Schloss and M. J. Yerna, *Annu. Rev. Physiol.*, 41, p. 703–722 (1979); R. J. Lasak, *Neurosci. Res. Program Bull.*, 19, p. 7–32 (1981); R. J. Lasek and M. L. Shelanski, *Neurosci. Res. Program Bull.*, 19, p. 3–153 (1981); C. A. Maretta, ed., *Neurofilaments* (1983); M. L. Shelanski and R. K. H. Liem, *J. Neurochem.*, 33, p. 5–13 (1979). Neurofilaments are composed of three proteins with molecular weights of 200,000, 150,000 and 70,000 daltons. B. H. Toh, L. J. Gibbs, Jr., D. C. Gajdusek, J. Goudsmit and D. Dahl, *Proc. Natl. Acad. Sci. USA*. An additional 62,000 dalton protein is also affiliated with the above-mentioned proteins. Such proteins are associated with slow axoplasmic transport. P. N. Hoffman and R. J. Lasek, *J. Cell Biology*, 66, p. 351–366 (1975).

Alzheimer's Disease, and other amyloid associated maladies including senile dementia, Down's syndrome, Pick's disease, progressive supranuclear palsy, multiple sclerosis and others, are characterized by the presence of one or more fused fibrils of repetitive amyloid beta proteins or other similar amyloid residues such as paired helical filaments, neurofibrillary tangles, neuritic plaques, amyloid plaques and cerebrovascular amyloidosis. B. H. Anderson, D. Breinberg and M. J. Downes, *Nature*, 298, p. 84–86 (1982). These paired helical filaments are indistinguishable immunologically and chemically from normal neurofilaments and share many of the same proteinaceous epitopes. B. H. Anderson, D. Breinberg and M. J. Downes, *Nature*, 298, p. 84–86 (1982); B. H. Toh, L. J. Gibbs, D. C. Gajdusek, J. Goudsmit and D. Dahl, *Proc. Natl. Acad. Sci. USA;* K. Iqbal, I. Grundke-Iqbal, H. M. Wisnieski and R. D. Terry, *Brain Res.*, 142, p. 321–332 (1975). It has been suggested that they interfere with axonal transport. P. N. Hoffman and R. J. Lasek, *J. Cell. Biol.*, 66, p. 351–366 (1975); J. W. Griffin, P. N. Hoffman, A. W. Clark, P. T. Carroll and D. L. Price, *Science*, 202, p. 633–665 (1978).

Using a cDNA clone of the gene encoding amyloid beta protein as a genetic probe, it was shown that the gene is located on chromosome twenty-one and is expressed in many tissues of the body. D. Goldjaber, M. I. Lerman, O. W. McBridge, U. Suffiotti and D. C. Gaidusak, *Science*, 235, p. 777–780 (1987); R. E. Tanzi, J. F. Gusella, P. C. Watkins, G. A. P. Bruns, P. St. George, M. L. Vankeuren, D. Patterson, S. Pagan, D. M. Kurnit and R. L. Neve, *Science*, 235, p. 880–884 (1987). Quantitation of amyloid beta protein expression, as seen by its mRNA levels using the cDNA probe, has revealed that its level of expression in brain tissue of Alzheimer's patients was not above that seen for other tissues outside the central nervous system. Such a finding was of interest to researchers when noting that amyloid plaque formation only occurs in the brain. R. E. Tanzi, J. F. Gusella, P. C. Watkins, G. A. P. Bruns, P. St. George, M. L. Vankeuren, D. Patterson, S. Pagan, D. M. Kurnit and R. L. Neve, *Science*, 235, p. 880–884 (1987).

Amyloid beta protein is obtained through conventional means known in the art and has been characterized in various reports. A. S. Cohen and E. Calkins, *Nature*, 183, p. 1202 (1959); A. S. Cohen and E. Calkins, *J. Cell Biology*, 21, p. 481 (1964); A. S. Cohen, E. Calkins and C. Levens, *Am. J. Pathol.*, 35, p. 979 (1959). More recent work is manifested by D. Caspi, M. C. Baltz and M. K. Pepys, *Mol. Biol. Med.*, 3, pp. 387–407 (1986); and D. Caspi, M. C. Baltz and M. K. Pepys, *Mol. Biol. Med.*, 3, pp. 409–424 (1986). Amyloid beta protein exists in various structural forms. The amyloid beta protein that has been experimentally used and as referred to herein in terms of any specific embodiments constitutes a mixture of such forms. It is to be understood that within the scope of the present invention, it is contemplated that any of the various forms of amyloid beta protein may be used.

Amyloid beta protein from the brain has been cDNA cloned and shown to contain a unique twenty amino acid $NH_2$-terminal sequence. Glenner, G. G. and Wong, W., *Biochem. Biophys. Res. Comm.*, 122, No. 3, pp. 1131–35 (1984); D. Caspi, M. C. Baltz and M. K. Pepys, *Mol. Biol. Med.*, 3, pp. 409–424 (1986); Goldgaber, D., Lennan, M. I., McBridge, O. W., Saffiotti, U. and Gaidusak, D. C., *Science*, 235, pp. 777–80 (1987).

It has been observed that a buildup of abnormally organized amyloid beta protein in brain tissue is manifested in Alzheimer's Disease. See Dennis J. Selkoe and Carmela R. Abraham, "Isolation of Paired Helical filaments and Amyloid Fibers from Human Brain," 134, *Methods in Immunology*, 388–404 (1986). The fact that there is an accumulation of beta amyloid protein in the brain in Alzheimer patients has been demonstrated by post mortem analysis of brain tissue that manifest a concentration of amyloid beta protein as part of an accumulation of parallel filaments or neural fibrillatory tangles in the brain that appear characteristic of Alzheimer victims, along with neuritic plaque and cerebral vasculatory amyloidosis.

The presence of amyloid beta protein in fibrils and plaques in Alzheimer's Disease, as well as other CNS disorders, has been suggested to be a result of a degradation product of the normal neurofilaments, D. Goldjaber, M. I. Lerman, O. W. McBridge, U. Sufflotti and D. C. Gaidusak, *Science*, 235, p. 777–780 (1987); R. E. Tanzi, J. F. Gusella, P. C. Watkins, G. A. P. Bruns, P. St. George, M. L. Vankeuren, D. Patterson, S. Pagan, D. M. Kumit and R. L. Neve, *Science*, 235, p. 880–884 (1987); M. Baudry, B. R. Dubrin, L. Beasley, M. Leon and G. Lynch, *Neurobiol. Aging*, 7, p. 255–260 (1986); G. G. Glenner, *Arch. Path. Lab. Med.*, 107, p. 218–282 (1983); or possibly due to improper metabolism of byproducts. Further breakdown products of amyloid beta proteins from neurofilaments have also been observed in amyloid plaques along meningeal vascular walls and intracortical blood vessels. S. Bahmanyar, E. J. Williams, F. B. Johnson, S. Young and D. C. Gaidusak, *J. Comp. Path*, 95, p. 1–5 (1985); M. E. Bruce and H. Fraser, *Neuropathol. Appl. Neurobiol*, 1, p. 189–207 (1981); M. E. Bruce and H. Fraser, *Neurophathol. Appl. Neurobiol.*, 7, p. 289–298 (1981); G. G. Glenner and W. Wong, J. Quaranta and G. G. Glenner, *Proc. Natl. Acad. Sci.*, 82, p. 8729 (1985); D. J. Selkoe, C. R. Abraham, M. B. Podlisky and L. K. Duffy, *J. Neurochem.*, 46, p. 1820 (1986).

During the mid-1960's, Solomon & Moos speculated that there was a close integration between immunological function, the central nervous system, psychophysiological factors (emotions), and disease, both physical and mental. G. F. Solomon and R. H. Moos, *Arch. Gen. Psychiatry*, 11, p. 657–674 (1964). The integration of those systems was initially suggested through observation of the presence of abnormal immunoglobulins in schizophrenic patients. G. F. Solomon and R. H. Moos, *Arch. Gen. Psychiatry*, 11, p. 657–674 (1964); J. G. Knight, *Lancet*, 82, p. 1073–1076 (1982); W. J. Fessel and M. Hirata-Hibi, *Arch. Gen. Psychiatry*, 9, p. 601–613. These immune aberrations (termed autoantibodies), which seemed to target certain body cellular structures, G. F. Solomon, *Psychoneuroimmunology*, p. 259–278 (1985); G. F. Solomon and R. H. Moos, *Psychosom. Mod.*, 27, p. 135–149 (1981), supported the concept that there is a close communication between the CNS and the immune system. For instance, met-enkephalin is a neurotransmitter in the CNS and is a product of activated T-helper cells. G. Zurawaki, M. Benedik, D. J. Kamb, J. S. Abrams, S. M. Zurawaki and F. O. Lee, *Science*, 232, p. 772–775 (1986).

The appearance of autoantibodies specific to the CNS neurofilaments in patients with Alzheimer's and other CNS disorders suggests that the body's immune system may play a role in the disease process. S. Bahmanyar, R. K. H. Liem, J. W. Griffin and D. C. Gajdusek, *J. Neuropathol. Exp. Neurol.*, 53, p. 85–90 (1984); S. Bahmanyar, M. C. Moreau-Dubois, P. Brown, F. Catala and D. C. Gajdusek, *J. Neuroimmunol.*, 5, p. 191–196 (1983); T. S. Elizan, J. Casals and M. D. Yahr, *J. Neurol. Sci.*, 59, p. 341–347 (1983). The autoantibodies against normal CNS neurofilaments react with the paired helical filaments in neurofibrillary tangles characteristic of Alzheimer's Disease. D. Dahl and A. Bignami, *Exp. Neurol.*, 58, p. 74–80 (1978); M. E. Bruce, *J. Neuropathol. Exp. Neurol*, 37, p. 595, abstract (1978).

Animal models for these CNS disorders, which are induced with aluminum chloride or B,B'-iminodipropionitrite (IDPN) to form paired helical filaments in neurofibrillary tangles, also react with antibodies directed against CNS neurofilaments. J. W. Griffen, P. N. Hoffman, A. W. Clark, P. T. Carroll and D. L. Price, *Science*, 202, p. 633–665 (1978).

Control of such autoimmune reactions may lead to the alleviation of symptoms manifested by such reactions. Over the past two decades, a body of clinical literature has accumulated relating to the treatment of autoimmune disease (or, more appropriately, diseases reflecting immune dysfunction) using a technique called provocative-neutralization therapy. Miller, *Annals of Allergy*, 38, p. 185–191 (1977); Miller, *Trans. Am. Soc. Opth. & Otolar. Allergy*, 14, p. 159–168 (1974); Miller, *Clinical Medicine*, 81, p. 16–19 (1974). In short, this method, which is commonly employed for allergy therapy, involves subcutaneous or sublingual introduction of an antigen known, or suspected, to provoke symptoms reflective of immune dysregulation. By serial titration of the provoking material, a concentration of that agent may be determined which will neutralize those symptoms induced by the same substance at a different concentration. That is a prime example of a dose-dependent phenomenon in which one dose induces a positive reaction while another dose of the same agent induces a negative response.

Although it is thought that neutralization occurs as a consequence of reestablishing homeostatic functional levels of T8 suppressor cells, it is quite possible that the same antigen used at a neutralizing concentration to reverse immune dysregulation could also, or instead, trigger endocrine and/or neuronal control mechanisms to reverse symptoms. Because of the intimate association between the three control systems (endocrine, immune, nervous) and proven communication pathways between and among the cells comprising these respective systems, a single active molecule, such as amyloid beta protein in the Alzheimer's victim, and related CNS disorders, may reverse symptoms via any or all of these routes.

Plaque formation is a common component in the etiology of numerous other disease as well. Principal among those are arteriosclerotic diseases. Like Alzheimer's and related diseases, arteriosclerotic diseases, such as atherosclerosis, are plaquing diseases. Such diseases are characterized by arterial plaque formation. These plaques commonly occur in large and medium-sized arteries and generally comprise cells, connective tissue (usually elastin, collagen, and glycosaminoglycans), and lipid deposits. The mixture of those components is usually complex, forming lesions which may be calcified in advanced stages of the disease. Plaque mass slowly increases throughout life, as blood vessels undergo progressive concentric fibromuscular thickening. In atherosclerotic patients, fibromuscular thickening of the intima of blood vessel walls proceeds rapidly and contributes, along with lipid deposition, to restricted blood flow. In non-atherosclerotic patients, the normal thickening of the walls of blood vessels does not contribute to increases in blood pressure and does not compromise blood flow. In fact, plaquing diseases often occur together and patients with neural plaques also have vascular plaques.

It is upon the matrix of fibromuscular thickenings that atherosclerotic plaques develop. Such plaques generally become more prevalent in the third decade of life, with localization being most common in the coronary arteries. Atherosclerotic lesions are generally thought to develop from fatty deposits which transiently occur in all humans in the developed muscular lining of blood vessels. The mechanism of transformation from fatty deposits or "streaks" to atherosclerotic lesions appears to be unknown. However, at least one report suggests that a virus may cause transformation of the normal lipid streaks to atherosclerotic plaques. Melnick, et al., *JAMA*, 263: 2204–207 (1990); wherein it was reported that an avian herpesvirus stimulated atherosclerotic lesions in chickens. The above-cited authors also correlated the presence of cytomegalovirus in humans with atherosclerotic lesions in humans. A finding of herpesvirus and cytomegalovirus antigens, as well as nucleic acids encoding those viruses, in arterial smooth muscle suggests that viral infection of arterial cells may be coincident with the development of atherosclerosis. However, a causative relationship between any virus and atherosclerosis has yet to be conclusively determined.

Of interest to the present invention is the chronic fatigue syndrome. Chronic fatigue syndrome is a disorder of which the major symptom is chronic, debilitating fatigue that is not resolved with bed rest, and which is severe enough to reduce daily activity below 50% for at least six months. In order to confirm diagnosis, eight of the following symptoms must have also begun at the onset of fatigue and have persisted or recurred over a period of at least six months. These symptoms include, mild fever, sore throat, painful lymph nodes, muscle weakness, muscle aches, fatigue after exercise, headaches, painful joints, neuropsychiatric complaints, sleep disturbances, and sudden onset in a healthy person. A diagnosis of chronic fatigue syndrome further involves elimination of a variety of other illnesses characterized by fatigue through personal history, physical examination and laboratory findings.

Chronic fatigue syndrome is a disorder that may have several causes. Much of the early literature on chronic fatigue syndrome focuses on the Epstein-Barr virus as a causative agent. The Epstein-Barr virus is a herpes-like virus that is the major cause of acute infectious mononucleosis, a common syndrome characterized by fever, sore throat, extreme fatigue, and swollen lymph glands.

It was later reported in the art that the rubella virus may have a possible role in the etiology of chronic fatigue syndrome. Studies conducted on patients having chronic fatigue syndrome have shown that many of those patients have abnormally high levels of antibody to the rubella virus.

The use of the influenza virus vaccine and the rubella virus vaccine both separately and together have been reported in the art for the treatment of herpes (Epstein-Barr virus) virus infections. Lieberman, *Clinical Ecology*, 7(3): 51 (1990) reported the use of patients suffering from Epstein-Barr virus with influenza virus vaccine given together with histamine and the immune enhancer Staphage lysate. Patients were also successfully treated with the same composition further in combination with rubella virus vaccine and with rubella virus vaccine alone.

Also of interest to the present invention is the disclosure of McMichael U.S. Pat. No. 4,521,405 that patients experiencing recurrent herpes simplex virus type II infection have reported relief of lesion pain and lesion enlargement upon treatment with compositions including histamine, measles inactivated, attenuated virus and influenza vaccine (killed) virus. McMichael, U.S. Pat. No. 4,880,626 taught a composition for alleviating the symptoms of AIDS comprising human chorionic gonadotropin, Staphage lysate, an influenza virus vaccine, such as Fluogen™ and fractionated inactivated HIV virus.

Also of interest to the present invention is hypertension. The increases in vascular permeability generally observed in hypertension may increase influx of lipoprotein into cells, thus increasing the likelihood of atheroma formation. Hypertension may also contribute to atherosclerosis in blood vessels surrounding the brain. A reduction in hypertension has been shown to significantly reduce the incidence of myocardial infarction associated with atherosclerosis. Other factors in the development and progression of atherosclerosis include diabetes mellitus, which may reduce lipid efflux from cells in the arterial wall. In addition, cigarette smoking dramatically increases the risk of developing atherosclerosis and associated hypertension, including their sequelae, such as infarction of the myocardium and brain. Obesity is another factor which may contribute, especially in an individual who smokes. Overall, hypertension is the single greatest risk factor in coronary diseases as well as cerebrovascular stroke.

The presence of hypertension is a primary indicator of an arteriosclerotic condition and is often used by physicians as the sole diagnostic measure of diseases such as atherosclerosis. Moreover, a reduction of blood pressure is thought to have an effect in reducing the severity of atheroma plaques. The mechanism for such reduction may be a reduction in the transport of lipids and proteins into blood vessels which is coincident with a reduction in blood pressure. The diastolic component of blood pressure is generally thought to be the primary indicator of hypertension. While the systolic component may vary greatly depending upon nervousness, anxiety and the like, diastolic blood pressure generally remains constant and is more reflective of a patient's general vascular state. A diastolic reading of over 90 is considered mild hypertension in an adult and a diastolic reading of over 100 is considered hypertensive and an indicator of arteriosclerotic disease.

SUMMARY OF THE INVENTION

The present invention provides methods for alleviating the symptoms of disease states associated with plaque formation. In accordance with the invention, there is provided a method to stimulate the appropriate metabolic regulatory systems (immune, CNS or endocrine) which retard the progress of the symptoms of plaquing diseases, such as Alzheimer's and related diseases and arteriosclerotic diseases. Observations by scientists have now indicated that the apparent elevated amyloid beta protein concentration in, for example, Alzheimer's diseases may not be due to an increase in genomic expression, but possibly to activation of a mechanism that induces the reorganization of amyloid moieties from normal neurofilaments into paired helical filaments resulting in neurofibrillary tangles, neuritic plaques or amyloid plaques. D. Goldjaber, M. I. Lerman, O. W. McBridge, U. Suffiotti and D. C. Gaidusak, *Science*, 235, p. 777–780 (1987); R. E. Tanzi, J. F. Gusella, P. C. Watkins, G. A. P. Bruns, P. St. George, M. L. Vankeuren, D. Patterson, S. Pagan, D. M. Kurnit and R. L. Neve, *Science*, 235, p. 880–884 (1987); M. Baudry, B. R. Dubrin, L. Beasley, M. Leon and G. Lynch, *Neurobiol. Aging*, 7, p. 255–260 (1986); G. G. Glenner, *Arch. Path. Lab. Med.*, 107, p. 218–282 (1983). The mechanisms of the present invention may result in triggering control processes that correct the rearrangement of neurofilaments, alter abnormal amyloid protein formation including amyloid beta formation, and/or allow for clearing of axonal transport mechanisms. Similarly, regulatory control systems, as noted above, play a role in arteriosclerotic plaque formation, leading to arteriosclerotic diseases such as atherosclerosis. A significant common occurrence in patients having arteriosclerotic disease and/or neural plaquing disease, such as Alzheimer's, is hypertension. Accordingly, methods of the present invention cause a reduction in hypertension as an indication of alleviation of the overall disease state. The diseases susceptible to treatment with methods according to the invention have in common plaque formation. Accordingly, treatment with methods according to the invention provides an effective treatment of all such diseases by alleviating causative symptoms of the disease. In addition, as detailed below, compositions and methods of the invention are useful in the reduction of hypertension generally.

As one aspect of the invention, it has been discovered that the component of influenza virus vaccines that provided activity against herpes viruses as reported in Lieberman, *Clinical Ecology*, McMichael U.S. Pat. No. 4,521,405 and McMichael U.S. Pat. No. 4,880,626 was not a portion of the killed virus such as a surface antigen, but rather was the preservative thimerosal which was present in commercially available influenza virus vaccines such as Fluogen™ (Parke Davis, Morris Plains, N.J.), Fluzone™ (Connaught Laboratories, Swiftwater, Pa.), and Flu-Immune™ (Lederle, Wayne, N.J.). Consequently, it is believed that results reported by McMichael and Lieberman attributed to the anti-herpes virus effects of influenza virus vaccine are due to the presence of thimerosal in the tested compositions. Further, it has been discovered that the anti-herpes virus activity of influenza virus vaccine is solely attributable to the presence of thimerosal in the tested vaccines and that herpes virus infections may be treated with thimerosal uncombined with or in the absence of influenza virus vaccine. Accordingly, the present invention provides methods for treating subjects suffering from herpes virus infections, comprising the step of administering an effective amount of a composition comprising thimerosal free of association with influenza virus. More specifically, the present invention provides methods for treating patients having chronic fatigue syndrome comprising administering an effective amount of thimerosal free of association with influenza virus to a subject suffering from chronic fatigue syndrome. The invention further provides methods for in vitro killing of herpes virus by administration of effective amounts of thimerosal. The invention further provides methods of treating plaquing diseases such as atherosclerosis and hypertension by combining thimerosal or thimerosal containing compositions such as influenza virus vaccines which contain thimerosal with amyloid beta protein.

In order to identify a dose of amyloid beta protein for use in the invention, a wheal produced upon intradermal injection of the therapeutic material was evaluated according to criteria set forth in Moore, Clinical Medicine, 81: 16–19 (1974), incorporated by reference herein. Upon subcutaneous injection, a wheal may be determined to be positive ten minutes after injection as a blanched, hard, raised, and discoid protrusion from the skin. A negative wheal is sufficiently absorbed at the end of ten minutes that the protrusion on the skin has grown less than an average of two millimeters in diameter from its original size.

In a preferred embodiment of the invention, compositions for treatment of plaquing diseases according to the invention comprise a dose from about $10^{-10}$ to about $10^{-2}$ mg of amyloid protein and from about 0.05 µg to 500 µg thimerosal with about 0.5 µg to about 50 µg thimerosal being preferred and about 5 µg thimerosal being particularly preferred. Alternatively, about 0.05 mL of between a 1:5 and 1:125 dilution of a thimerosal containing influenza virus vaccine in saline may be used. Thus, the total volume of a typical composition according to the invention for administration to a patient is about 0.05 cc, or one drop. Compositions according to the invention for treatment of plaquing diseases may comprise β-amyloid protein or the first 28 amino acids of β-amyloid protein.

Preferred dosages of thimerosal for treatment of subjects suffering from herpes virus infections range from about 0.05 µg to 500 µg thimerosal with about 0.5 µg to about 50 µg thimerosal being preferred and about 5 µg thimerosal being particularly preferred.

Also in a preferred embodiment, compositions according to the invention are pharmaceutical compositions for treatment of arteriosclerotic diseases which pharmaceutical compositions comprise amyloid protein and thimerosal in a pharmaceutically-acceptable carrier.

Methods according to the present invention are useful in alleviating symptoms of arteriosclerosis generally, and atherosclerosis in particular. Such methods comprise the step of administering to a patient suspected or confirmed as having an arteriosclerotic disease an effective amount of a pharmaceutical composition comprising amyloid protein and an influenza virus vaccine. An effective amount of a composition according to the invention is an amount which results in a reduction in the symptoms of an arteriosclerotic disease. Most preferably, an effective amount of a composition according to the invention comprises from about $10^{-10}$ to about $10^{-2}$ mg of an amyloid protein, preferably β-amyloid protein, and about 0.05 mL of between a 1:5 and 1:125 dilution of an influenza virus vaccine. An amyloid protein used in methods according to the invention may be a β-amyloid protein or may be the first 28 amino acids of a β-amyloid protein. A highly preferred amount of amyloid protein used in compositions and methods according to the invention is from about $10^{-5}$ and about $10^{-2}$ mg of amyloid protein.

Methods and compositions according to the present invention are effective in alleviating symptoms of any disease in which plaquing is involved and especially diseases in which atheroma formation is characteristic. Compositions and methods according to the invention also alleviate hypertension and reduce cholesterol, both of which have a direct effect in reducing the severity of or eliminating symptoms associated with arteriosclerotic disease. The following detailed description of the invention provides exemplification of claimed methods and compositions. However, it is understood by the skilled artisan that other uses of the invention, specifically relating to the treatment of arteriosclerotic diseases, are within the scope of the present claims.

Methods according to the present invention are useful in alleviating symptoms of arteriosclerosis generally, and atherosclerosis in particular. Such methods comprise the step of administering to a patient suspected or confirmed as having an arteriosclerotic disease an effective amount of a pharmaceutical composition comprising amyloid protein and an influenza virus vaccine. An effective amount of a composition according to the invention is an amount which results in a reduction in the symptoms of an arteriosclerotic disease. Most preferably, an effective amount of a composition according to the invention comprises from about $10^{-10}$ to about $10^{-2}$ mg of an amyloid protein, preferably β-amyloid protein, and about 0.05 cc of between a 1:5 and 1:125 dilution of a commercially available thimerosal containing influenza virus vaccine. Preferred dosages of thimerosal for treatment of subjects suffering from herpes virus infections range from about 0.05 µg to 500 µg thimerosal with about 0.5 µg to about 50 µg thimerosal being preferred and about 5 µg thimerosal being particularly preferred. An amyloid protein used in methods according to the invention may be a β-amyloid protein or may be the first 28 amino acids of a β-amyloid protein. A highly preferred amount of amyloid protein used in compositions and methods according to the invention is from about $10^{-5}$ and about $10^{-2}$ mg of amyloid protein.

Methods and compositions according to the present invention are effective in alleviating symptoms of any disease in which plaquing is involved and especially diseases in which atheroma formation is characteristic. Compositions and methods according to the invention also alleviate hypertension and reduce cholesterol, both of which have a direct effect in reducing the severity of or eliminating symptoms associated with arteriosclerotic disease. The following detailed description of the invention provides exemplification of claimed methods and compositions. However, it is understood by the skilled artisan that other uses of the invention, specifically relating to the treatment of arteriosclerotic diseases, are within the scope of the present claims.

Also in a preferred embodiment, the invention provides a method for alleviating the symptoms of disease states associated with abnormal accumulation of and/or molecular organization of amyloid protein or amyloid plaques, which comprises administration to a diseased patient of an effective amount of amyloid protein or an effective active fragment thereof. The amyloid protein is preferably an amyloid beta protein although amyloid protein fragments such as fragments comprising the first 28 amino acid residues of the amyloid beta protein are expected to be useful. The method of the invention is useful against disease states associated with abnormal accumulation of and/or molecular organization of amyloid protein or amyloid plaques including disease states in which the amyloid protein or plaques are associated with the central nervous system and histopathologically related disorders. Such diseases include, but are not limited to Alzheimer's Disease and Parkinson's Disease. Other disease states include those such as atherosclerosis.

DETAILED DESCRIPTION OF THE INVENTION

A. Application of Materials and Methods of the Invention to the Treatment of Alzheimer's and Related Diseases The alleviation of Alzheimer's Disease symptoms observed following administration of amyloid beta protein as described herein likely reflects stimulation of appropriate metabolic regulatory systems in the Alzheimer's Disease patients such that accumulation and/or formation of the paired helical filaments in neurofibrillary tangle and/or amyloid plaque developments are significantly altered or slowed and accumulated proteins are eliminated. This reprogramming to establish proper homeostasis would allow more efficient transmission of nerve impulses which would result in clinical improvement of treated Alzheimer's patients.

Typically, a pharmaceutical dosage unit of the present invention for the delivery of amyloid beta protein in a low concentration comprises a liquid or solid carrier and an effective amount of amyloid beta protein. One suitable carrier for sublingual administration comprises a phenylated saline solution. Effective amounts of the amyloid protein range from about $10^{-10}$ to about $10^{-2}$ mg, and preferably from about $10^{-5}$ to about $10^{-3}$ mg and most preferably about $10^{-4}$ mg, amyloid beta protein in association with pharmaceutically acceptable excipients. The amyloid beta protein is administered through standard methods, including sublingual, subcutaneous and transdermal routes, and in dosage units that are either liquid or solid.

One explanation for the mode of action of this invention may be that the amount of this protein administered is sufficient to trigger a negative feedback mechanism to the body such that production of additional amyloid beta protein, possibly through breakdown of normal neurofilaments, is inhibited. Under this theory, the low level of amyloid beta protein, or a derivative thereof, gives a signal to the body to correct the abnormal synthesis/degradation process. The body sensors are then adjusted to normal metabolic control of amyloid beta protein processing that allows the proper balance to reestablish itself, alleviating the abnormal processing. The immune system, as well as the endocrine and CNS control systems, could play an integral regulatory role in response to the low dose therapy, with the amyloid protein functioning through mechanisms that not only correct the molecular organization of the amyloid beta protein moieties, but clear the interfering amyloid molecular constructs.

In a preferred embodiment, the present invention provides administration of amyloid beta protein or a derivative thereof. The amyloid beta protein may be provided either as part of a liquid solution or in a solid powder matrix, and may be administered with conventional excipients to permit ease of administration and accurate dosage delivery. Patients characterized herein below were evaluated using a battery of objective tests designed to measure cognitive ability. These included the mini-mental State Examination, the Verbal Fluency Task Examination (word name task and category task), evaluation on the Demattis Dementia Rating scale, and the Word-Association Task Examination of the Wechster Memory Scale-Revised. Not all results of all tests are provided herein, however, the results of all the tests were qualitatively the same as those below and led to the same conclusions as those provided herein relative to the effect of treatment according to the invention.

EXAMPLE 1

A 67 year old male with a history of Alzheimer's Disease for four years prior to initiating therapy presented with an inability to answer questions, to place names with faces, and to complete his sentences. His wife noted a consistent downhill progression of his condition on a monthly basis. At the initiation of therapy, with the composition of the invention, his initial score on the Mini-Mental State Exam was 5 of a possible 30. The subject was treated by sublingual administration four times per day of a dosage unit comprising $10^{-4}$ mg of amyloid beta protein in a phenylated saline solution. After five months of therapy according to the invention, the patient scored a 12½ on the Mini-Mental State Exam, was reading road signs while travelling and was communicating with family members. Also, the patient appeared to be more relaxed and better able to respond to his wife's efforts to assist him.

EXAMPLE 2

An 81 year old male with a history of Alzheimer's Disease was treated according to the invention. Prior to treatment the subject was unable to dress himself, had a flat affect, was poorly communicative and scored 10½ on the Mini-Mental State Exam. The subject was treated by sublingual administration four times daily of the amyloid beta dosage unit of Example 1. After three months of treatment, the subject scored 17 points on the Mini-Mental State Exam, was more animated in speech, could dress himself most days and was more confident in physical actions.

EXAMPLE 3

In this example, the subject was a 62 year old female who was originally diagnosed by the University of Pittsburgh Medical School Alzheimer's Disease Research Center to be suffering from a fulminating form of Alzheimer's Disease. In one year, the subject had gone from being director of nursing in a chronic care establishment to requiring constant care. The subject was unable to communicate, did not appear to recognize anyone and had a score of 1.5 on the Mini-Mental State Exam. The subject was treated by sublingual administration four times daily of the amyloid beta dosage unit of Example 1. After three months of treatment, the patient's husband reported that warmth had returned to the patient's hands, no deterioration of any type was evident, although prior to therapy, he could note weekly declines. Communication remained difficult but improved for the subject, she showed increased alertness, and she was not only able to recognize individuals consistently, but also was able, at times, to participate in conversations, and her test score rose to 7.75 on the Mini-Mental State Exam. Although the subject was originally diagnosed as having Alzheimer's Disease, the results of an autopsy indicated that she did not have Alzheimer's Disease but suffered from a form of Parkinson's Disease known as Striatonigral degeneration.

EXAMPLE 4

In this example, the subject was a 79 year old male who had suffered from two transient ischemic attacks and had also been diagnosed as having Alzheimer's Disease. Prior to treatment, the subject had a score of 16 on the Mini-Mental State Exam. The subject was treated by sublingual administration four times daily of the amyloid beta dosage unit of Example 1. While the subject became somewhat more irascible and eventually died of a stroke two months after the trial period, his performance on various mental performance exams including the Dementia Rating Scale improved during the initial six month evaluation period. Specifically, the Mini-Mental State Exam improved during the initial six months of testing with scores of 18, 20, 21 and 25 at the three, four, five and six month tests, respectively. The subject's mental performance at the three month follow-up examination had declined significantly, with the score on the Mini-Mental State Exam dropping to the level of the original test with a score of 16. The subject's scores on the other mental performance exams also showed marked decline to the original performance levels. The subject died of a stroke prior to the six-month follow-up evaluation.

EXAMPLE 5

In this example, a 76 year old male who was diagnosed as having Alzheimer's Disease, was treated by sublingual administration four times daily of the amyloid beta dosage unit of Example 1. The subject's performance on both the Mini-Mental State Exam and the Dementia Rating Scale improved significantly over five months of testing. Test scores on the Mini-Mental State Exam on the first, third, fourth and fifth months were: 20, 20, 20 and 25; while scores on the Dementia Rating Scale were: 115, 117, 122 and 126. The subject showed improvement primarily in areas of attention and conceptualization and in immediate short term memory, with some improvement in verbal fluency. In contrast, his performance did not improve in the area of delayed memory which remained severely compromised. In addition, there was only slight improvement demonstrated on tasks requiring new learning abilities which was also severely compromised. The subject was unavailable for follow-up study.

EXAMPLE 6

In this example, the subject was a 74 year old woman who was diagnosed as having Alzheimer's Disease so advanced that she was unable to identify a comb or a key. The subject was disoriented, incontinent and severely hypertensive and required intensive around the clock care from her sister who was a nurse. The subject was treated by sublingual administration four times daily of the amyloid beta dosage unit of Example 1. The subject's initial score on the Mini-Mental State Exam was 2, and the subject demonstrated slight improvements (subsequent scores were 2, 3, 4, 8 and 7) although some, but not all, of the improvement may have resulted from modification of the test procedure to accommodate the marked expressive language deficits exhibited by the subject. Significantly, the subject's blood pressure returned to normal upon treatment with the amyloid protein composition. This indicates that the amyloid protein composition exhibits utility in treatment of the symptoms of atherosclerosis which can be associated with amyloid plaques.

B. Application of Materials and Methods to the Treatment of Arteriosclerotic Diseases Alzheimer's patients treated with amyloid protein as described above show a significant decrease in blood pressure as a result of such treatment which is concomitant with a reduction in symptoms of dementia. As noted above, Melnick, et al. report a role for a herpesvirus (Cytomegalovirus, CMV) in atherogenesis. In co-owned, U.S. Pat. No. 4,880,626, it is noted that, while all untreated AIDS patients studied had CMV, none of the patients treated with a influenza vaccine based (Fluogen™) composition had CMV. The present application teaches compositions and methods comprising the anti-plaquing amyloid protein and the anti-viral thimerosal in order to effect treatment of patients presenting with arteriosclerotic conditions. The following examples provide exemplification of the invention through representative embodiments comprising the use of claimed compositions and methods on human subjects. For each example below, original (i.e., pretreatment) blood pressure was taken about three times during each reading to ensure accuracy. Subsequent measures were repeated about 5 times. Unless otherwise noted, patients undergoing treatment according to the invention received 1 drop (sublingual) four times per day. One drop is approximately 0.05 mL of a composition according to the invention.

EXAMPLE 7

A 54-year-old male patient presented with atherosclerosis, including blood pressure of 140/90. The patient was treated with sublingual drops of a composition comprising $10^{-9}$ mg amyloid protein in a 1:25 dilution of 0.05 mL thimerosal containing influenza vaccine (Fluogen™) in saline. The patient was not treated with any other medication during the period in which he was treated with the above composition. In addition, the patient reported that he remained on a high fat diet and reported no exercise during the treatment period. After daily sublingual treatment (1 drop 4 times per day) for 90 days, the patient's blood pressure had decreased to 117/72. After two years of taking the above composition, the patient's blood pressure has stabilized at about 115/70. The patient's cholesterol also significantly decreased after sustained treatment.

EXAMPLE 8

A 44-year-old, moderately obese male presented with blood pressure of 140/110. The patient was treated with daily sublingual doses (4 times daily) of a composition according to the invention, as recited above in Example 8. The patient received no other medication and did not otherwise alter his lifestyle during the treatment period with the result that his blood pressure had decreased to 120/90. After continued treatment as described above and with no change in lifestyle or diet during the treatment period, the patient had a blood pressure of 123/78. Blood pressure was taken up to five times during each measurement to ensure accuracy.

EXAMPLE 9

A 55-year old female with initial (pretreatment) blood pressure of about 138/90 began treatment according to methods of the invention and with compositions according to the invention. The patient showed a steady improvement in the diastolic component of blood pressure through three months of treatment. At that point, the patient discontinued treatment and three months later showed increases in diastolic blood pressure. Upon resuming treatment, diastolic blood pressure again decreased. During treatment, the patient was administered compositions as described above in Examples 7 and 8. The following table provides a partial tracking of the patient's blood pressure during treatment and non-treatment periods.

TABLE 1

| Treatment | Blood Pressure |
|---|---|
| pre-treatment | 138/90 |
| yes | 150/88 |
| yes | 144/82 |
| no | 136/82 |
| no | 118/74 |
| no | 122/80 |
| no | 142/86 |
| yes | 140/80 |
| yes | 130/78 |

EXAMPLE 10

A 50-year-old male patient presented with blood pressure of 150/104 and began treatment as described above. The results of that treatment are presented in Table 2.

TABLE 2

| Treatment | Blood Pressure |
|---|---|
| yes | 146/95 |
| yes | 155/94 |
| yes | 138/90 |
| yes | 138/78 |
| yes* | 150/98 |
| yes* | 140/96 |
| yes* | 156/108 |
| no | 160/102 |
| no | 160/100 |
| yes | 130/78 |

*dose of 1-2 drops/day

The results presented in Examples 9 and 10 demonstrate not only the effect of compositions according to the invention in reducing symptoms of arteriosclerosis, but also demonstrate that such symptoms return upon cessation of treatment according to the invention.

EXAMPLE 11

A 76-year-old female with blood pressure of 210/110 began treatment according to the invention and as described above, using 4 drops per day. After one month of treatment, the patient's blood pressure was reduced to 200/90. After 90 days of treatment her blood pressure was reduced to 160/90.

EXAMPLE 12

According to this example veterinary clinical trials were carried out involving the administration of amyloid beta protein and a thimerosal containing fraction of influenza virus vaccine for the treatment of atherosclerosis in a rabbit atherosclerosis model. Specifically, a filter centrifugation technique was used to isolate a 30 kD fraction of commercially available influenza virus vaccine (Fluviron™) containing thimerosal as a preservative at a concentration of 0.01% wherein the vaccine was loaded onto an Ultrafree low-binding spin-filter unit with a 30,000 nominal molecular weight limit and centrifuged in a microfuge until all of the fluid had passed through the filter. The filtrate was further filtered through a 5,000 nominal molecular weight spin filter to yield a thimerosal containing 5 kD filtrate fraction.

According to the trial, four groups of six atherosclerosis-prone Watanabe rabbits apiece were treated with A) saline as a control; B) a composition according to the invention comprising $10^{-4}$ mg of amyloid beta protein and the 5 kD thimerosal containing influenza virus vaccine fraction; C) a composition according to the invention comprising $10^{-3}$ mg amyloid beta protein and the 5 kD thimerosal containing influenza virus vaccine fraction; and D) a composition according to the invention comprising $10^{-4}$ mg of amyloid beta protein and the 5 kD thimerosal containing influenza virus vaccine fraction. The animals were treated for six months at which time the surviving animals were tested for weight gain and two animals for each group were sacrificed and vessel patency was determined by a gross pathological examination of plaque formation in the lumen of the aorta. The animals treated with the compositions of the invention had clear bifurcations and exhibited fewer and smaller plaques than did the control animals which were aged and sex matched and which exhibited plaque accumulation and occlusion of vessels exiting the aorta. The average weight gain over six months for the control animals was 690 grams as compared to the three test groups which showed, respectively, average weight gains of 450 grams (Group B); 450 grams (Group C); and 525 grams (Group D).

EXAMPLE 13

According to this example, a U.S. FDA Phase ½ controlled double blind human clinical trial was conducted using thimerosal containing compositions for the treatment of chronic fatigue syndrome. Thirty-six (36) patients suffering from documented chronic fatigue syndrome were studied of whom thirty-three (33) completed the study. Of the subjects who completed the study, 17 were treated with placebo and 16 were treated by sublingual administration six times daily of 1 drop (0.05 mL) of a composition comprising 0.0020 mL (2 µL) of a influenza vaccine containing 0.01 % (0.2 µg) thimerosal, 0.0004 mL (0.4 µL) rubella virus vaccine and 0.0576 mL saline. After ten weeks of treatment, the subjects were evaluated and were taken off of either the drug or placebo and were further evaluated after an additional four weeks of no treatment.

The subjects were evaluated by means of two principal art recognized efficacy parameters: (1) a visual analogue scale for subjective evaluation of fatigue, and (2) a fatigue impact scale comprising 36 questions related to cognitive, psychologic and social disorders. Analysis of the results using the visual analogue scale showed no statistically significant difference at the 95% confidence level between the therapy and the control. Analysis of the results using the fatigue impact scale also failed to demonstrate a statistically significant difference at the 95% confidence level between the therapy and placebo groups but did indicate a trend in favor of the therapy over the placebo indicative of a therapeutic effect.

C. Application of Materials and Methods of the Invention to the Treatment of Herpes Infections The following examples relate to work establishing the in vitro and in vivo anti-herpes viral activity of thimerosal as the anti-herpes active fraction of influenza virus vaccines.

Typically, a pharmaceutical dosage unit of the present invention for the delivery of thimerosal comprises a liquid or solid carrier and an effective amount of thimerosal. One suitable carrier for sublingual administration comprises a phenylated saline solution. Effective amounts of thimerosal range from about 0.05 µg to 500 µg thimerosal with about 0.5 µg to about 50 µg thimerosal being preferred and about 5 µg thimerosal being particularly preferred. The thimerosal is preferably administered in association with pharmaceutically acceptable excipients. The thimerosal is administered through standard methods, including sublingual, subcutaneous and transdermal routes, and in dosage units that are either liquid or solid.

EXAMPLE 14

According to this example, a filter centrifugation technique was used to isolate a 30 kD fraction of commercially available influenza virus vaccines (Fluviron™ and Fluzone™) wherein the vaccine was loaded onto an Ultrafree low-binding spin-filter unit with a 30,000 nominal molecular weight limit and centrifuged in a microfuge until all of the fluid had passed through the filter. In vitro assays with the 30 kD filtrate fractions (which contained thimerosal present at a concentration of 0.01% as a preservative in the commercial vaccine) saw complete inhibition of herpes virus in cell culture assay utilizing HSV-1 and HSV-2 infection of A549 (Human Lung Carcinoma) cells in vitro. The fraction obtained was also used in place of dilute influenza virus vaccine in human subjects and was found to improve the clinical response to chronic fatigue syndrome and other herpes infections.

EXAMPLE 15

According to this example, a further filtration was carried out isolating a 5 kD fraction from the Fluvirin™ influenza vaccine. This fraction which also contained thimerosal was effective at inhibiting growth of the herpes virus in the cell culture of Example 14 and appeared to clinically superior in in vivo administration to 30 kD fraction of Example 14.

In the following set of examples 16 through 21 the 30 kD thimerosal containing influenza vaccine isolate was administered to subjects suffering from herpes virus infections.

EXAMPLE 16

In this example, a 38 year old female presented with acute onset of pain on the left side of the head, neck, shoulder, chest and arm which she had suffered for five days. She also suffered from similar pain on the dorsal left foot. Examination revealed three small papular lesions in a quarter-sized red area on the left upper chest. Herpes zoster was suspected. The 30 kD thimerosal containing fraction of example 15 was administered sublingually with one drop (0.05 mL) four times daily for a dosage of about 5 μg thimerosal. The subject reported a 95% reduction in pain 30 to 60 minutes after administration of the thimerosal containing fraction. The subject continued to do well after one week of QID treatment with one drop of the composition.

EXAMPLE 17

In this example a 66 year old female with a history of recurrent herpes zoster presented during the initial stages of such an outbreak. Administration of one drop sublingually of the composition of Example 16 eliminated discomfort. The subject took a second drop of the composition 24 hours later and did not experience further pain or discomfort for the next two weeks.

EXAMPLE 18

In this example a 19 year old male presented with a history of having developed acute infectious mononucleosis approximately five days previously with symptoms of sore throat, 4+ fatigue, lymph node enlargement (4+ cervical), headache, dizziness, splenomegaly. The subject was treated with one subcutaneous injection of 0.2 mL of the composition of example 16 and reported 60–70% improvement within 30 minutes. Seven hours later, the subject reported feeling 90% better.

EXAMPLE 19

According to this example a 30 year old woman presented with predictable oral herpes simplex outbreak on the 23rd day of her menstrual cycle. Associated with the herpes outbreak were premenstrual syndrome symptoms which were sufficiently severe as to require anti-psychotic medication. The patent administered 2 drops of the composition of Example 16 sublingually at the first sign of herpes outbreak (that being sensitivity of the lip in the area of the typical lesion expression). No cold sores developed in or on her mouth for the first time in several years and the premenstrual syndrome was not exhibited.

EXAMPLE 20

A 63 year old female subject with a history of lesions lasting several weeks presented with a four day old HSV-1 lesion on her lip. One drop of the composition of example 16 was administered sublingually and within 30 minutes the subject reported a marked improvement. The lesion resolved in two days with administration of two drops of the composition per day.

EXAMPLE 21

A 50 year old plus male presented with chronic fatigue syndrome having pronounced lethargy, a history of mental fogginess and poor quality of life. Two drops of the composition of example 16 were administered to the subject sublinqually and the subject reported improvement in excess of 70% with an increase in energy and mental clarity for the first time in several years. After three weeks, the subject continued to do well with administration of two drops of the composition daily.

EXAMPLE 22

According to this example, a wide variety of tests were carried out to determine the anti-herpes active component of the 5 kD influenza vaccine fraction with the result that it was determined that thimerosal possesses the anti-herpes effect. In vitro assays with purified thimerosal demonstrate activity against herpes viruses. Of interest is the observation that when thimerosal is mixed in a test tube with herpes virus and is subsequently introduced into susceptible cells viral propagation is not inhibited. This suggests that the anti-herpes viral activity of thimerosal is not by direct action on the virus. Further study shows that thiosalicylic acid and dithiodibenzoic acid which are the breakdown products of thimerosal do not provide antiviral activity in vivo although dithiodibenzoic acid shows anti-herpes virus activity in vitro.

The foregoing representative results demonstrate that application of compositions according to the invention reduce blood pressure and other symptoms associated with arteriosclerosis. Therefore, treatment methods and compositions according to the invention constitute an effective means for alleviating the symptoms of arteriosclerotic diseases and for completely alleviating such diseases in some cases.

What is claimed is:

1. A method for alleviating the symptoms of disease states associated with amyloid plaque formation selected from the group consisting of Alzheimer's disease or Parkinson's disease comprising the step of administering to a patient in need thereof an effective amount of amyloid protein.

2. The method of claim 1 wherein the amyloid protein is an amyloid beta protein.

3. The method of claim 1 wherein the amyloid protein is a fragment comprising the first 28 amino acid residues of the amyloid beta protein.

4. The method of claim 1 wherein from about $10^{-10}$ to about $10^{-2}$ mg of amyloid protein is administered per dose.

5. The method of claim 1 wherein from about $10^{-5}$ to about $10^{-3}$ mg of amyloid protein is administered per dose.

6. The method of claim 1 wherein the disease state is Alzheimer's Disease.

7. The method of claim 1 wherein the disease state is Parkinson's Disease.

8. The method of claim 1 wherein said effective amount of amyloid protein or a therapeutically-active fragment thereof is administered to a patient in need thereof in a composition also comprising thimerosal.

9. The method of claim 8, wherein said composition comprises from about $10^{-10}$ to about $10^{-2}$ mg of amyloid protein and from about 0.05 µg to about 500 µg thimerosal.

10. The method of claim 9 wherein said composition is administered to a patient in an amount of about 0.05 cc of the composition.

11. A pharmaceutical composition for treatment of disease states associated with abnormal accumulation or molecular organization of amyloid protein or amyloid plaques selected from the group consisting of Alzheimer's disease or Parkinson's disease which comprises amyloid protein or a therapeutically active fragment thereof in an amount effective to alleviate one or more symptoms of said disease state and a suitable carrier.

12. The pharmaceutical composition of claim 11 wherein the amyloid protein is amyloid beta protein.

13. The pharmaceutical composition of claim 11 wherein the amyloid protein is a fragment comprising the first 28 amino acid residues of the amyloid beta protein.

14. The pharmaceutical composition of claim 11 in the form of a single dosage unit which comprises from about $10^{-10}$ to about $10^{-2}$ mg of amyloid beta protein in association with pharmaceutically acceptable excipients.

15. The pharmaceutical composition of claim 11 further comprising an effective amount of thimerosal.

16. The pharmaceutical composition of claim 14; wherein said composition comprises from about $10^{-10}$ to about $10^{-2}$ mg of amyloid protein and from about 0.05 µg to about 500 µg of thimerosal.

* * * * *

UNITED STATES PATENT AND TRADEMARK OFFICE
CERTIFICATE OF CORRECTION

PATENT NO. : 5,753,624

DATED : May 19, 1998

INVENTOR(S) : McMichael et al.

It is certified that error appears in the above-identified patent and that said Letters Patent is hereby corrected as shown below:

On the title page: Item [54] and Column 1, line 2,

"Disease" should be --Diseases--.

Item [56]

References cited, U.S. PATENT DOCUMENTS, Patent No. 4,666,829, "Colenneo et al." should be --Glenner--.

References cited, OTHER PUBLICATIONS, Bahmanyar et al., "Serum Antibodies to Neurofilament Antigens in Patients with Neurological and Other diseases and in Healthy cControls," *J. Neuroimmunol*, 5:191-196 (1983), in the title of the article, "cControls" should be --Controls--.

References cited, OTHER PUBLICATIONS, Page 2, Samet, Peptides Offer Promise for Ttreating Alzheimer's and other Neurodiseases, *Genetic Engineering News*, p. 24 (Jul./Aug. 1991), quotation marks should be before "Peptides" and after "Neurodiseases" and "Ttreating" should be --Treating--.

References cited, OTHER PUBLICATIONS, Page 2, Miller, J.B., "The Importance of Herpes Virus Infections and the Ability to Neutralize Them," Relief at Last: Neuetralizations for food Allergy and Other illnesses, "Ch. 9" should be --Ch. 29--.

References cited, OTHER PUBLICATIONS, the following references should be added: --Allen, "Is RA27/3 Rubella Immunization a Cause of Chronic Fatigue?", *Medical Hyoptheses*, 27:217-220 (1988); Anderton et al., "Monoclonal antibodies show that neurofibrillary tangles and neurofilaments share antigenic determinants," *Nature*, 298:84-86 (July 1, 1982); Bahmanyar et al., "Amyloid Plaques in Spongiform Encephalopathy of Mule Deer," *J. Comp. Path.*, 95:1-5 (1985)--.

Column 2, line 40, "Lennan" should be --Lerman--.

Column 4, line 23, "disease" should be --diseases--.

Column 10, line 9, "Wechster" should be --Weschsler--.

UNITED STATES PATENT AND TRADEMARK OFFICE
CERTIFICATE OF CORRECTION

PATENT NO. : 5,753,624
DATED : May 19, 1998
INVENTOR(S) : McMichael et al.

It is certified that error appears in the above-identified patent and that said Letters Patent is hereby corrected as shown below:

Column 16, line 32, "sublinqually" should be --sublingually--.

Column 12, line 49, "8" should be --7--.

Signed and Sealed this

Twenty-sixth Day of September, 2000

Attest:

Q. TODD DICKINSON

*Attesting Officer*      *Director of Patents and Trademarks*